United States Patent [19]
Jones

[11] Patent Number: 5,866,914
[45] Date of Patent: Feb. 2, 1999

[54] RADIATION BEAM SHAPING DEVICE

[75] Inventor: Andrew D. Jones, Everett, Wash.

[73] Assignee: Northwest Medical Physics Equipment, Inc., Everett, Wash.

[21] Appl. No.: 784,347

[22] Filed: Jan. 15, 1997

[51] Int. Cl.⁶ .................................................. G21K 1/02
[52] U.S. Cl. ...................... 250/505.1; 378/145; 378/161
[58] Field of Search ........................ 250/505.1; 378/140, 378/145, 161

[56] References Cited

U.S. PATENT DOCUMENTS 5,524,041   6/1996   Grenier ................................ 250/505.1

OTHER PUBLICATIONS

Northwest Medical Physics, Point Reference System, Frameless Stereotactic Radiotherapy Comprehensive System Brochure, May 1996 . No Pages.
Northwest Medical Physics, Point Reference System, Frameless Stereotactic Radiotherapy Remote Treatment Planning Brochure, May 1996 . No pages.
Brenner, David J. and Eric J. Hall, "Stereotactic Radiotherapy of Intracranial Tumors—An Ideal Candidate for Accelerated Treatment," *Int. J. Radiation Oncology Biol. Phys.* 28(4):1039–1041, 1994.
Jones, D. et al., "A Frameless Method for Stereotactic Radiotherapy," *British Journal of Radiology* 66:1142–1150, Dec. 1993.
Jones, D. et al., "Frameless Stereotactic Multiple Arc Radiotherapy," *Cancer Consult*, May 1993, pp. 65–68.
Northwest Medical Physics Center—Lynnwood, Washington, S.M.A.R.T. Hardware Software Installation instructions, one page, May 1993.
Reike, J.W. et al., "Accommodation for Spatial Uncertainties in Radiosurgery," Division of Radiation Oncology, Virginia Mason Medical Center, Seattle, Washington, and Northwest Medical Physics Center, Lynnwood, Washington, 1991.

*Primary Examiner*—Kiet T. Nguyen
*Attorney, Agent, or Firm*—Seed and Berry LLP

[57] ABSTRACT

A system for shaping a radiation beam exiting from a radiation source. The system includes a mount coupleable to the radiation source. The mount has a beam aperture with a tapered inner surface extending through the mount, through which the radiation beam passes. The system further includes a die having a tapered outer surface capable of engaging the tapered inner surface of the beam aperture. The die has a beam window extending through the die which is substantially transparent at at least a selected radiation power such that the radiation emerging from the beam window has the same size and shape as the beam window.

35 Claims, 3 Drawing Sheets ns914

RADIATION BEAM SHAPING DEVICE

TECHNICAL FIELD

The present invention is directed toward beam shaping devices and, more particularly, toward beam shaping devices for use with radiation therapy systems.

BACKGROUND OF THE INVENTION

Radiation therapy is often used to treat patients having malformations such as benign and malignant tumors. In a typical radiation treatment program, a radiation beam of sufficient strength is repeatedly focused on the targeted tumor for a selected period of time. Over the course of several treatment sessions, the focused radiation beam kills tumor cells, ultimately eliminating the tumor. One problem with radiation treatment is that the radiation is harmful to the healthy tissue surrounding the tumor. The radiation must pass through the healthy tissue surrounding the tumor in order to reach the tumor, and over the course of time, the healthy tissue suffers adverse effects and may eventually be damaged or destroyed as a result of repeated exposure to the radiation beam. The tissues surrounding brain tumors, such as the optic nerve, auditory nerves, and the brain stem are particularly susceptible to damage by radiation.

One solution to the above problem has been to irradiate the tumor from a range of angles by moving the patient and the source of the radiation relative to each other. As the radiation beam and the patient move relative to each other, the tumor remains within the beam's width, while at each angle a different portion of the surrounding tissue is irradiated by the beam. In this manner, the radiation required to treat the tumor passes through a greater number of regions of surrounding tissue, which reduces the amount of radiation absorbed by any one region and minimizes the likelihood that the healthy surrounding tissue will be damaged by the radiation.

One problem with the above method of radiation treatment is that it is preferably fractionated to include a series of radiation doses spread out over the course of several days, weeks or months. During each radiation treatment session, the patient and particularly the tumor must be precisely aligned relative to the radiation source in order to ensure that the tumor and only a minimum amount of surrounding tissue are irradiated by the radiation beam. Typically, frame-type devices have been used to fix the position of the patient's head relative to the radiation beam source. These devices are screwed directly into the patient's skull. The target is then located with respect to the frame device. The frame device is cumbersome, uncomfortable, and was not intended to be left on the patient for more than one treatment session, making fractionated treatment impossible.

To solve the positioning problem described above, the assignee employs a frameless stereotactic system. This system uses three metallic markers which are permanently placed in the patient's skull and which define a three-dimensional coordinate system. An imaging device precisely locates the tumor relative to the markers prior to the first therapy session. Once the position of the tumor relative to the markers is known, the radiation beam may be positioned relative to the permanently placed markers rather than the frame device.

In a typical installation of the system described above, the radiation beam passes from the radiation source through a collimator which focuses or directs the beam. The focused beam is then directed to the tumor. The collimator includes a removable die with an aperture therethrough which is used to shape and size the radiation beam, particularly for irregularly shaped tumors. For example, the die may have an aperture that has a size and shape which matches a silhouette of the irregularly shaped tumor when the tumor is viewed from a particular angle. When the tumor is irradiated by the radiation beam at that angle, only the tumor and surrounding tissue directly in the path of the beam are exposed to the beam. When the beam source and collimator are moved so as to irradiate the tumor from a different angle, the die is removed from the collimator and a new die having an aperture corresponding to a silhouette of the tumor when viewed from the new angle is inserted.

SUMMARY OF THE INVENTION

Typically, the dies used with existing frameless stereotactic systems are cylindrical and fit within a cylindrical aperture in the collimator. One drawback of the cylindrical dies is that they are difficult to accurately and releasably position within the collimator. If the dies fit too tightly within the collimator, they may become stuck within the collimator aperture because, for example, the collimator and the dies have different rates of thermal expansion. If the dies fit too loosely within the collimator, they change position as the collimator and radiation source rotate about the patient's head. The die ceases to accurately position the radiation beam relative to the tumor, and the beam unnecessarily irradiates and damages healthy tissue surrounding the tumor. Even if the cylindrical die is firmly clamped to the collimator, for example with a series of set screws, the position of the die relative to the collimator and therefore relative to the patient may be different from one therapy session to the next depending on the order in which the set screws are tightened or the degree to which the set screws are tightened.

The present invention provides a system for shaping a radiation beam exiting from a radiation output port of a radiation source. The system shapes the radiation beam so that a target of the beam may be irradiated from a variety of angles without unnecessarily irradiating material surrounding the target. In a preferred embodiment of the present invention, the system includes a mount coupled to the radiation source at an output port from which the radiation beam emanates. The mount has a beam aperture with at least two openings and a tapered inner surface extending between the two openings. The system further comprises a die having a beam window extending through the die. The beam window is substantially transparent at at least a selected radiation energy. A tapered outer surface of the die is capable of engaging the tapered inner surface of the beam aperture.

The invention also provides a method for manufacturing a die usable for shaping a radiation beam and irradiating a target from at least a selected angle. The method comprises shaping a column of material to have a selected cross-sectional shape. The material is substantially transparent to the radiation beam at a selected radiation beam energy. The column of material is placed within a die shell leaving a gap between the column and an inner surface of the die shell. The die shell outer surface has a tapered shape that is removably engageable with a tapered aperture of a radiation beam source. The gap between the column and the die shell is filled with a mold material that is substantially opaque at at least the selected radiation beam energy. The gap is filled with mold material such that the ends of the column remain exposed through the shell ends. The die may then be placed in the path of a radiation beam such that the column is aligned with the radiation beam, and the shape of the beam emerging from the die has the same shape as the cross section of the column.

DETAILED DESCRIPTION OF THE INVENTION

A tapered beam shaping device for shaping a radiation beam is described in detail herein. In the following description, numerous specific details are set forth such as the specific means by which components are coupled, the specific shapes of the components, etc., in order to provide a thorough understanding of the present invention. One skilled in the relevant art, however, will readily recognize that the present invention can be practiced without these specific details or can readily be altered to include other coupling means, shapes, etc. than those described herein. In other instances known structures are not shown or described in detail in order to avoid obscuring the present invention.

Figure 1:
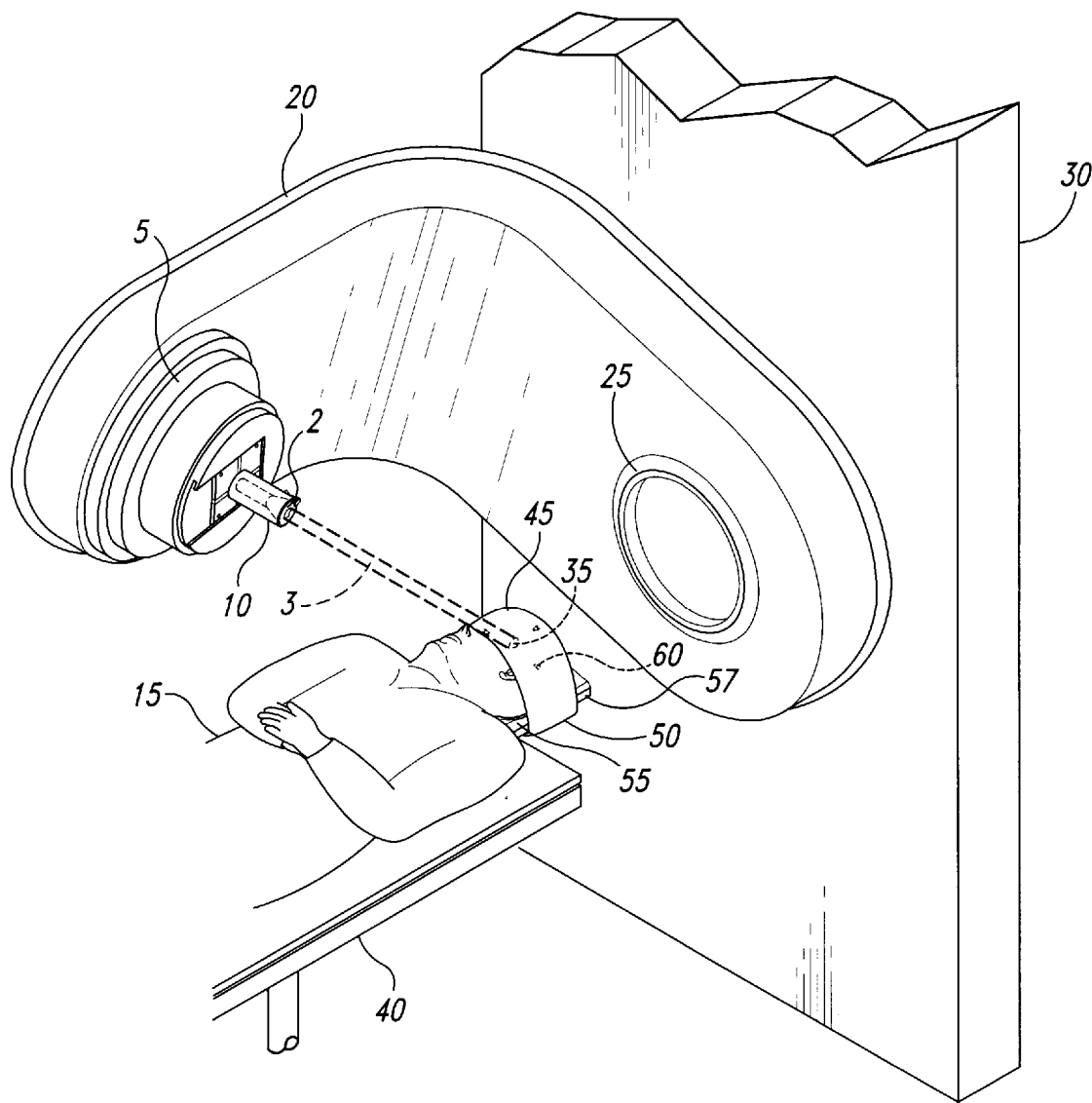
FIG. 1 is an isometric view of a patient and the present invention installed in a radiation source which is rotatable about the head of the patient.

As shown in FIG. 1, a tapered beam shaper 2 shapes and sizes the cross section of a radiation beam 3 emanating from a beam source 5. The radiation beam 3 passes from the beam source 5 through a collimator 10, through the tapered beam shaper 2, and is directed toward a patient 15. The beam source or linac 5 is positioned on an arm 20 which is attached at a pivot joint 25 to a fixed frame 30. The arm 20 and beam source 5 are pivotable about the patient 15 and direct the radiation beam 3 toward a tumor 35 located within the patient' head.

As shown in FIG. 1, the patient is positioned on a couch 40 which is translatable and rotatable relative to the beam source 5 and the arm 20. Because both the arm 20 and the couch 40 are movable relative to each other, the radiation beam 3 may be directed toward the tumor 35 from a wide range of angles. The patient's head is secured to an immobilization board 57 by a conformal mask 50 and a conformal headrest 55. The immobilization board is attached to the couch 40 with releasable plungers. Screws 60 are fixedly positioned in the patient's skull and serve as points of reference by which a user (not shown) directs the radiation beam 3 toward the tumor 35.

Figure 2:
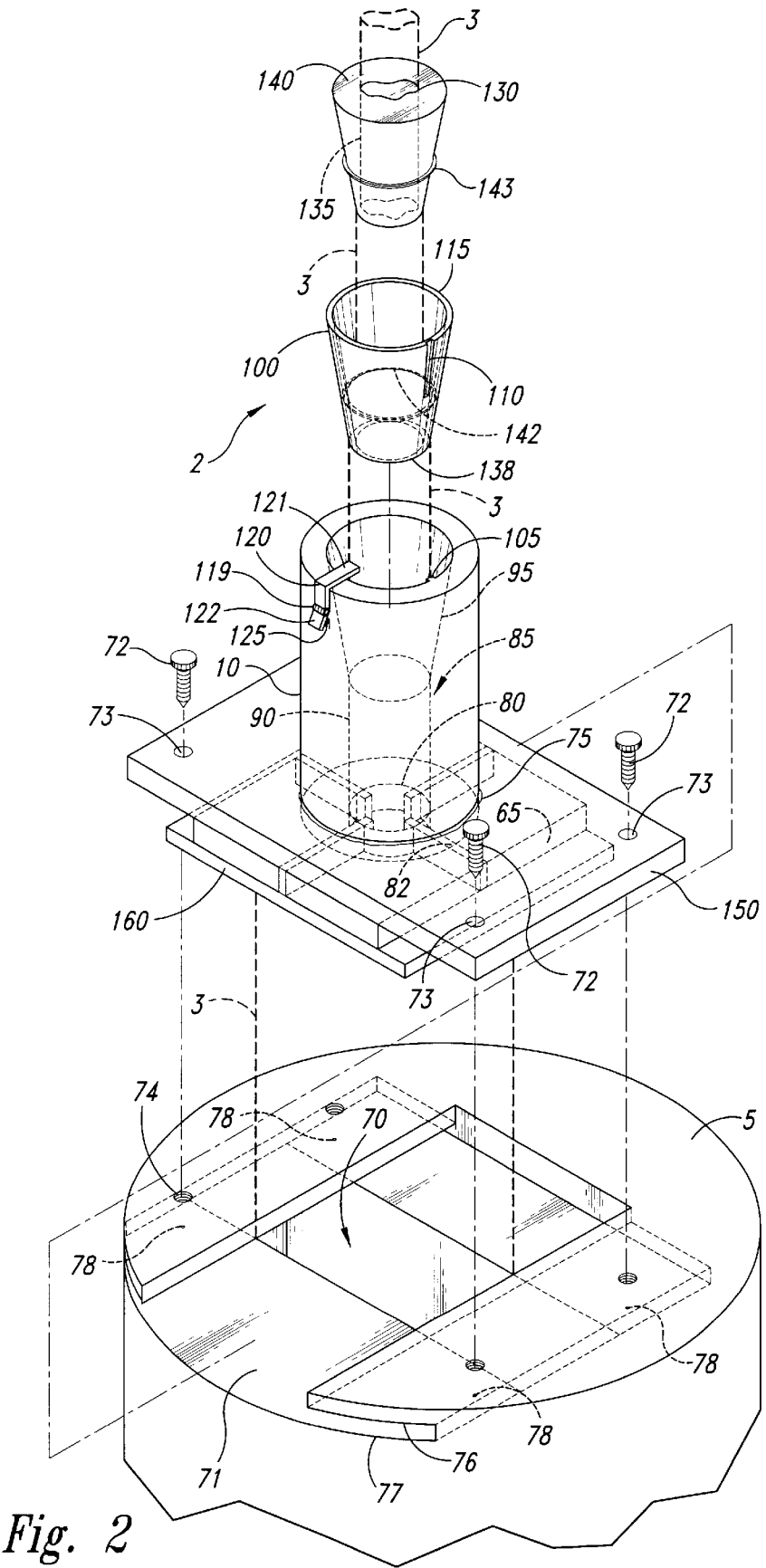
FIG. 2 is an exploded isometric view of the device of the present invention.

As shown in greater detail in the exploded view of FIG. 2, the tapered beam shaper 2 is slideably and releasably mounted in the collimator 10, which in turn is slideably and releasably mounted to the beam source 5. The beam source 5, collimator 10 and beam shaper 2 each have axially aligned apertures therethrough which direct and shape the radiation beam 3.

The beam source 5 has a rectangular aperture 70 through which the radiation beam 3 is emitted. A slot 71 extends from one side of the rectangular aperture 70 to an outer edge of the beam source 5 and is shaped to engage a slat 160 projecting outwardly from beneath a base 65 of the collimator 10. A coupling plate 150 extends outwardly from above the base 65. The collimator 10 is welded at a weld joint 75 to the collimator base 65. The base 65 is welded to the slat 160 and coupling plate 150. The collimator 10 is releasably attachable to the beam source 5 by sliding the slat 160 into the slot 71, such that the slat passes between a slot upper surface 76 and a slot lower surface 77. Pointed screws 72 are passed through holes 73 in the coupling plate 150, and are threaded into threaded holes 74 located adjacent to the collimator aperture 70 to secure the collimator 10 to the beam source 5. The pointed screws 72 engage divots 78 located beneath the threaded holes 74 to align the collimator 10 with the beam source 5. In alternate embodiments of the present invention, the collimator 10 is screwed directly to the beam source 5 without the use of slots or slats. Further embodiments include other devices known in the art for releasably securing the collimator 10 to the beam source 5.

The collimator base 65 contains a base aperture 80 which passes completely through the base and is aligned with the rectangular aperture 70 and which permits the radiation beam 3 to pass from the beam source 5 into the collimator 10. Four position markers 82 project from the base 65 a short distance into the base aperture 80. The position markers 82 are preferably of a material which is opaque to the radiation beam 3 so that the position markers create four distinct shadows on photographic images produced with the radiation source. The shadows assist the user in orienting the contents of the images relative to the radiation source 5.

The collimator 10 has a collimator aperture 85 which passes completely through the collimator and is aligned with the base aperture 80. The collimator aperture 85 includes a cylindrical aperture portion 90 which is located adjacent to the base aperture 80 and a tapered aperture portion 95 located at the opposite end of the collimator 10 and adapted to engage the beam shaper 2.

The tapered beam shaper 2 is sized and shaped to be removably positioned within the tapered aperture portion 95 of the collimator aperture 85. The tapered beam shaper 2 has a tapered outer shell 100 which is shaped to slideably and firmly engage the tapered aperture portion 95 of the collimator 10. The tapered outer shell 100 contains a tab slot 110 which is shaped to removably engage a tab 105 projecting inwardly from the collimator 10 into the tapered aperture portion 95. During installation, the beam shaper 2 is oriented so that the tab slot 110 engages the tab 105 when the tapered beam shaper 2 is inserted into the collimator 10, orienting the beam shaper relative to the collimator. In an alternate embodiment, the tab slot 110 is located in the collimator 10 and the tab 105 is located in the beam shaper 2.

The tapered outer shell 100 has a lip 115 which projects outwardly from the collimator aperture 85 when the tapered beam shaper 2 is installed therein. The lip 115 is positioned to allow the user to grasp the tapered beam shaper 2 when moving the tapered beam shaper into or out of the collimator aperture 85. A latch 120 is pivotally mounted at a pivot 119 to the collimator 10 and is moveable between an engaged position and a disengaged position. A spring 125 biases the latch toward the engaged position. In the engaged position, the latch 120 extends over the lip 115 of the tapered beam shaper 2 when the tapered beam shaper is installed in the collimator aperture 85. In the disengaged position, the latch 120 is moved away from the lip 115 by pressing a lever portion 122, allowing the tapered beam shaper 2 to be removed from the collimator 10. In a preferred embodiment, the latch 120 includes a flexible portion 121 which is sufficiently flexible to fit firmly over a variety of lips 115 which protrude from the collimator 10 by varying amounts, yet is sufficiently rigid to prevent the tapered beam shaper 2 from slipping out of the collimator when the collimator and arm 20 are in an inverted position.

The tapered shell 100 is filled with a mold material 140 which is opaque to the radiation beam 3. A circumferential slot 142 located on the inner surface of the tapered shell 100 is shaped to engage a corresponding circumferential tab 143 located on the outer surface of the mold material 140, preventing the mold material from sliding out of the tapered shell. A shaper aperture 130 extends through the mold material 140 from one end of the tapered shell 100 to the other. As shown in FIG. 2, the cross-sectional shape of the shaper aperture 130 is the same shape as a silhouette of the tumor 35 (FIG. 1) when the tumor is viewed from a selected target angle. The shaper aperture 130 is filled with an insert 135 which is transparent to the radiation beam 3. When the tapered beam shaper 2 is positioned within the collimator aperture 85, the radiation beam 3 passes from the radiation source 5 through the rectangular aperture 70, the base aperture 80, the collimator aperture 85, the shaper aperture 130 and the insert 135, and emerges from the beam shaper 2 with the same cross-sectional shape as the shaper aperture 130, the insert 135 and the silhouette of the tumor 35.

The shaper aperture 130 and insert 135 are shown in FIG. 2 with parallel sides. In an alternate embodiment, the sides of the shaper aperture 130 and insert 135 diverge from a lower edge 138 of the tapered shell 100 to the lip 115. In a further alternate embodiment, the divergence of the shaper aperture 130 and insert 135 correspond to a divergence of the radiation beam 3.

In a preferred embodiment, the radiation beam 3 can have a power of 6 MV. The mold material 140 comprises Cerrobend, a low melting point alloy which includes lead, bismuth, cadmium, and tin, available from Med Tec of Iowa City, Iowa. In a further aspect of the preferred embodiment, the mold material 140 has a length of 4 inches, which is sufficient to block more than 97% of the portion of the 6 MV radiation beam 3 aligned with the mold material. The tapered beam shaper therefore transmits only that portion of the radiation beam 3 having the desired cross-sectional shape.

In a preferred embodiment, the insert 135 is formed from Styrofoam manufactured by Dow Chemical Co., Inc. and available from Med Tec of Iowa City, Iowa. The Styrofoam is transparent to the radiation beam 3 at power settings of 4–20 MV and may be easily shaped to match the silhouette of the tumor 35. In alternate embodiments, alternate materials having the desired properties of opacity and transparency form the mold material 140 and insert 135, respectively, in beam shapers used with radiation beams having a power of 6 MV and other values known to those skilled in the art.

The operation of the beam shaper of the present invention is best understood by reference to FIGS. 1 and 2. As shown in FIG. 1, three screws 60 are permanently placed in the patient's head 45 in an outpatient procedure. In a preferred embodiment, the screws 60 are conventional titanium cortex screws. The shanks of the screws 60 are hollowed out to accommodate a short length of gold wire which shows up clearly on megavoltage X-ray film. During a pre-treatment session, the patient is fitted with a conformal headrest 55 that is individually shaped to fit between the patient's head 45 and the immobilization board 57. In a preferred embodiment the headrest 55 is formed from conventional foams, though in alternate embodiments, other materials known to those skilled in the art are used. An individually shaped mask 50 is shaped to wrap around the upper portion of the patient's head 45 and the immobilization board 57 to firmly and releasably affix the patient's head to the immobilization board. In a preferred embodiment, the mask 50 is formed from a thermoplastic which is wrapped around the patient's head 45 and the immobilization board while in a warm, flexible state and is permitted to harden to the desired shape. The mask 50 substantially immobilizes the patient's head relative to the radiation beam source 5.

The aperture 130 of each individual beam shaper 2 is determined by a three-dimensional treatment planning computer. This is done by first performing an imaging study, commonly CT or MRI. The patient's head shape and the locations of all structures of interest, such as tumors, optic nerves, auditory nerves, and the brain stem are clearly defined. This information is then input into the planning computer and the apertures 130 are defined. A series of tapered beam shapers 2 are then constructed. Each tapered beam shaper 2 has an aperture 130 and an insert 135 that have a cross-sectional shape substantially identical to the shape of the tumor 35 when viewed from one of the target angles determined during the imaging study.

During a treatment session, the patient is placed on the couch 40 with the conformal headrest 55 positioned between the immobilization board 57 and the patient's head 45. The mask 50 is placed over the patient's head 45 and affixed to the immobilization board 57, which is in turn affixed to the couch 40 to immobilize the patient's head relative to the couch. The collimator 10 is installed in the beam source 5 by sliding the slat 160 into the slot 71 and tightening the screws 72 into the threaded holes 74, as shown in FIG. 2. Using the screws 60 in the patient's head, the tumor 35 is brought to the focal point, or isocenter, of the radiation source 5. The tapered beam shaper 2 corresponding to the first of the series of target angles is inserted into the collimator 10 such that the tab 105 located on the collimator 10 engages the tab aperture 110 located on the outside of the tapered beam shaper 2. In this manner, the position of the tapered beam shaper 2 relative to the tumor 35 is fixed so that the position of the shaper aperture 130 and insert 135 correctly match the silhouette of the tumor 35 when viewed from the first target angle. The tapered beam shaper 2 is inserted a sufficient distance into the collimator 10 such that the spring-loaded latch 120 snaps over the rim 115 of the tapered beam shaper to lock the tapered beam shaper into place.

When the tapered beam shaper 2 is locked into place, the outer shell 100 of the tapered beam shaper firmly engages the tapered portion 95 of the collimator aperture 85. The snug fit between the tapered beam shaper 2 and the collimator 10 ensures that the tapered beam shaper will not loosen from the collimator 10 and will not move when the collimator and the beam source 5 are rotated during the course of a treatment session.

Several factors, including thermal expansion, may cause the tapered beam shaper 2 to move axially relative to the collimator 10 or to have a different axial location relative to the collimator from one treatment session to the next. Such misalignments will not affect the accuracy with which the radiation beam targets the tumor 35 because the shaper aperture 130 and the insert 135 which shape the radiation beam are axially symmetric. The flexible portion 121 of the latch 120 is capable of engaging a range of tapered beam shapers 2 having rims 115 positioned over a range of distances from the collimator 10.

Once the tapered beam shaper 2 has been positioned within the collimator 10 and latched into place with the latch 120, the beam source 5 is rotated to the first target angle relative to the tumor 35. The beam source 5 is activated for a prescribed period of time, generating the radiation beam 3. The radiation beam 3 passes from the beam source 5 into the collimator aperture 85. The beam then passes into the tapered beam shaper 2. Because only the insert material 135 is transparent to the radiation beam 3, the shape of the beam emerging from the tapered beam shaper 2 is identical to the cross-sectional shape of the insert 135 and the tumor 35 when viewed from the first target angle.

When the desired dose of radiation has been administered to the patient, the radiation beam source 5 is turned off and the user removes the tapered beam shaper 2 from the collimator 10 by moving the latch 120 away from the lip 115, grasping the lip 115 projecting from the collimator aperture 85, and pulling the tapered beam shaper 2 free from the collimator 10. A new tapered beam shaper 2 having an insert 135 which corresponds to a silhouette of the tumor 35 when viewed from a second target angle is then placed in the collimator 10 and latched into place with the latch 120. The beam source 5 is moved to the second target angle and a second radiation dose is administered to the patient. The above process is repeated for a selected number of target angles and tapered beam shapers 2. At each target angle, a tapered beam shaper 2 having the desired insert 135 is placed within the collimator 10 prior to positioning the beam source 5 and administering the desired radiation dose. By targeting the tumor from a range of angles with a shaped radiation beam, the amount of radiation absorbed by any one portion of tissue surrounding the tumor is reduced.

In a preferred embodiment, the aperture outer shell 100 and the inner walls of the collimator aperture 85 are formed from aluminum. The tapered aperture portion 95 and outer shell 100 are tapered at approximately 5° and have circular cross-sections. In alternate embodiments, the tapered aperture portion 95 and outer shell 100 are tapered at an angle which is at least 2° greater or less than the angle by which the radiation beam 3 diverges. In this manner, any gap between the outer shell 100 and the tapered aperture portion 95 will not be aligned with the diverging radiation beam 3, minimizing any extraneous radiation which passes completely through the gap. Such extraneous radiation reduces the focus of the radiation beam 3.

Further alternate embodiments include other materials, taper angles and cross-sectional shapes which permit the beam shaper 2 to be easily installed and removed from the collimator 10. In one such embodiment, the outer shell is eliminated so that the mold material 140 slideably engages the tapered aperture portion 95 of the collimator aperture 85. In a further alternate embodiment, the insert 135 is eliminated, leaving the shaper aperture 130 open for radiation transmission.

As shown in FIGS. 1 and 2, the slat 160 slides directly along the surfaces of the slot 71 into which it fits, and the beam shaper 2 slides directly along the surface of the tapered aperture portion 95. In an alternate embodiment, the slat 160 and/or the beam shaper 2 contain bearings, such as ball bearings or roller bearings, which engage the slot 71 and the tapered aperture portion 95, respectively, minimizing the frictional wear of the beam source 5, collimator 10 and beam shaper 2. Other embodiments employ other friction-reducing means known to those skilled in the art.

Figure 3:
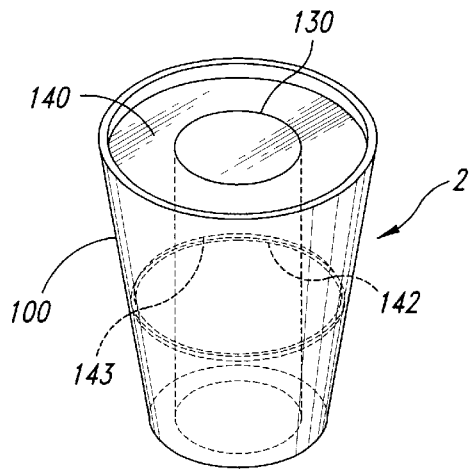
FIG. 3 is an isometric view of an alternate embodiment of the present invention.

The shaper aperture 130 and insert 135 are shown in FIG. 2 as having a cross-sectional shape which is substantially identical to the cross-sectional shape of the tumor 35 when viewed from a selected target angle. In an alternate embodiment illustrated in FIG. 3, the tapered beam shaper 2 includes a cylindrical shaper aperture 130. Cylindrical shaper apertures 130 may be used for treatment of tumors 35 that have a substantially spherical shape or where a low potential for damage to surrounding tissue does not warrant a specially-shaped shaper aperture 130 and insert 135. As shown in FIG. 3, the alternate embodiment of the tapered beam shaper 2 does not include a tab for positioning the tapered beam shaper relative to the collimator 10 because the shaper aperture 130 is radially symmetric. The alternate embodiment also does not include an insert, and may be manufactured by boring the mold material 140 to form the aperture 130. Tapered beam shapers 2 having shaper apertures 130 with circular cross sections need not be tailored to a particular tumor 35 and may be produced in a number of standard sizes.

Figure 4:
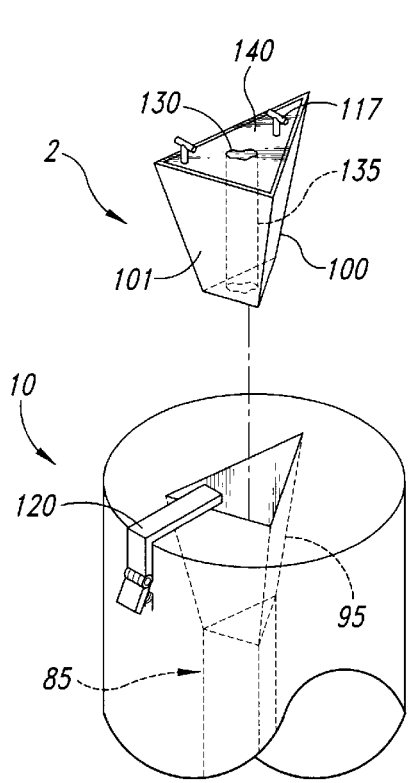
FIG. 4 is an isometric view of an alternate embodiment of the present invention wherein a tapered beam shaper and corresponding collimator aperture have non-circular cross-sections.

FIG. 4 illustrates a further alternate embodiment of the present invention in which the beam shaper 2 and collimator 10 have non-circular cross-sectional shapes. The collimator 10 has a tapered aperture portion 95 shaped similarly to that of the shell 100. In this manner the beam shaper 2 may be releasably inserted into the correspondingly shaped aperture portion 95 of a collimator 10 as discussed above in reference to the embodiments illustrated in FIGS. 1–3.

As illustrated in FIG. 4, faces 101 of the shell 100 slide along similarly shaped faces of the tapered aperture portion 95 when the tapered beam shaper 2 engages the collimator 10. The faces 101 are oriented so that the tapered beam shaper 2 may be placed into the tapered aperture portion 95 of the collimator 10 in only one orientation. In this manner, the need for tabs and tab apertures to orient the tapered beam shaper 2 relative to the collimator 10 and the tumor 35 is eliminated. Although the cross-sectional shape of the shell 100 illustrated in FIG. 4 is triangular, the shell 100 has any of a myriad of cross-sectional shapes in alternate embodiments.

In the embodiment illustrated in FIG. 4, the tapered beam shaper 2 includes handles 117 which project upwardly from the surface of the mold material 140. The handles 117 permit the user to easily grasp the tapered beam shaper 2 for removal from and insertion into the collimator 10.

Figure 5:
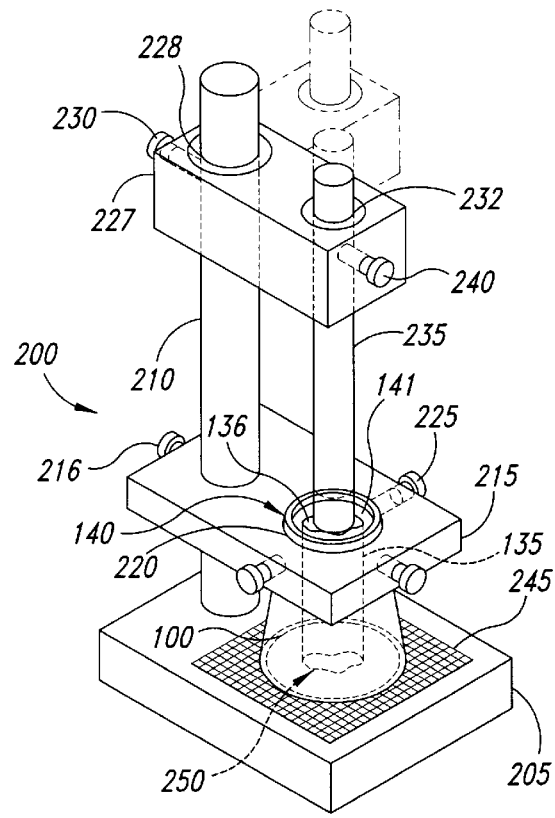
FIG. 5 is an isometric view of an apparatus used to manufacture a beam shaping device in accordance with an embodiment of the present invention.

FIG. 5 illustrates a manufacturing jig for manufacturing the tapered beam shaper 2 of the present invention. The jig 200 includes a base 205 and a retainer positioning rod 210 projecting upwardly from the base. A shell holder 215 is movable toward and away from the base 205 and may be fixed in a selected location by tightening an adjustment thumbscrew 216. The shell holder has a shell aperture 220 therethrough which is shaped to accommodate the shell 100 of the tapered beam shaper 2 of the present invention. Shell thumbscrews 225 are threadably mounted into holes positioned within the shell holder 215 around the shell aperture 220 and are adjustable to engage and disengage the shell 100 in a conventional manner. The base 205 is adapted to retain a flat graph 245 such as a conventional sheet of graph paper which includes a full-size silhouette 250 of the tumor 35 when viewed from a selected target angle. The silhouette 250 is used to position the insert 135 relative to the shell 100, as is discussed below.

A retainer block 227 is moveably positioned on the retainer positioning rod 210, above the shell holder 215. The retainer positioning rod 210 passes through a hole 228 in the retainer block 227. A retainer block thumbscrew 230 is threadably mounted to the retainer block 227 and is adapted to engage and disengage the retainer positioning rod 210 in a conventional manner. The retainer block 227 may be moved along the retainer positioning rod 210 toward and away from the shell holder 215 and may be swiveled clockwise or counter-clockwise around the retainer positioning rod between a centered position shown in solid lines in FIG. 5 and an off-center position shown in phantom lines.

The retainer block 227 has an aperture 232 through which is slideably mounted a retainer rod 235. The retainer rod 235 is moveable through the aperture 232 toward and away from the base 205 and may be temporarily fixed in a conventional manner at a selected position relative to the base 205 with a retainer rod thumbscrew 240. The retainer rod 235 is movable between a raised position in which it is out of contact with the insert 135 as shown in phantom lines in FIG. 5 and a lowered position where it retains the insert 135 in a fixed position relative to the base 205 and the shell 100, as shown in solid lines in FIG. 5.

In operation, the retainer rod thumbscrew 240 is loosened and the retainer rod 235 is moved to its raised position. The retainer rod thumbscrew 240 is then tightened to hold the retainer rod 235 in its raised position. The retainer block thumbscrew 230 is loosened and the retainer block 227 is rotated to the off-center position shown in phantom in FIG. 5. When the retainer block 227 is in the off-center position, the retainer rod 235 is positioned away from the shell holder 215 to permit access to the shell holder 215 and the base 205. The graph 245 containing the silhouette of the tumor 35 is placed upon base 205 and the shell 100 is placed within the aperture 220. The graph 245 is positioned beneath the shell 100 such that the silhouette 250 is roughly centered within the shell 100. The graph 245 is then fixed to the base 205 and the shell 100 is affixed to the shell holder 215 by tightening the shell thumbscrews 225.

Figure 6:
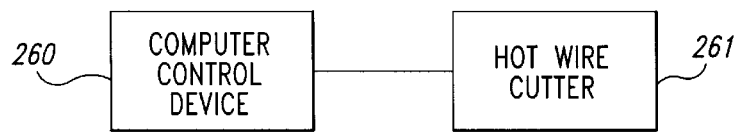
FIG. 6 is a schematic of a computer-controlled cutting device for cutting aperture inserts in accordance with an embodiment of the present invention.

The insert 135 is carefully shaped to have the same cross-sectional shape over its entire length as the silhouette 250 located on the graph 245. The insert 135 may be manufactured using a standard hot wire Styrofoam block cutter such as is available from the Huestis Corporation of Bristol, R.I. In an alternate manufacturing method the insert 135 is shaped with a computer control device as shown schematically in FIG. 6. FIG. 6 illustrates a computer control device 260 which controls a hot wire cutter 261. In an alternate embodiment, the computer control device 260 and the hot wire cutter 261 may be combined in a stand-alone unit.

The insert 135 is placed within the shell 100 and positioned on the silhouette 250. The retainer block thumbscrew 230 is then loosened and the retainer block 227 and the retainer rod 235 are rotated as a unit such that the retainer rod 235 is positioned over the insert 135 as shown in solid lines in FIG. 5. The retainer block thumbscrew 230 is tightened, fixing the position of the retainer block 227 relative to the base 205. The retainer rod thumbscrew 240 is then loosened and the retainer rod 235 lowered, until it firmly contacts the insert 135. The retainer rod thumbscrew 240 is then tightened, fixing the position of the retainer rod 235 relative to the insert 135. With the insert 135 held firmly in place relative to the base 205, liquid mold material 140 is poured into the gap formed between the insert 135 and the outer shell 100. A sufficient quantity of mold material is poured into the shell 100 so as to fill the gap between the insert 135 and the shell 100, such that the upper surface 141 of the mold material is flush with the end 136 of the insert 135. The end 136 of the insert 135 and the upper surface 141 of the mold material 140 are recessed below the lip 115 of the shell 100 so as to prevent the user from inadvertently contacting and damaging the insert 135.

Once the mold material 140 has had an opportunity to cool, the tapered beam shaper 2 is removed from the jig 200.

The retainer rod thumbscrew 240 is loosened, the retainer rod 235 is moved from its lowered position to its raised position and the retainer rod thumbscrew retightened. The retainer block thumbscrew 230 is loosened and the retainer block 227 is swiveled from the centered position shown in solid to the off-center position shown in phantom in FIG. 5. The retainer block thumbscrew 230 is then re-tightened with the retainer block 227 in the off-center position. The shell thumbscrews 225 are loosened and the tapered beam shaper 2 removed from the shell holder 215.

As discussed previously, the insert 135 is formed from Styrofoam in a preferred embodiment. In addition to being transparent to radiation at selected powers, Styrofoam is not affected by exposure to the liquid mold material 140. In alternate embodiments, the insert 135 is formed from other materials known to those skilled in the art which are easily shaped, which are unaffected by exposure to liquid mold material 140, and which are transparent at 4–20 MV or other selected radiation beam energies.

As discussed previously, the insert 135 may be eliminated from the beam shaper 2, leaving the shaper aperture 130 open for transmission of radiation. In an alternate embodiment of the method described herein, particularly appropriate for embodiments such as those illustrated in FIG. 3, the entire shell 100 is filled with the mold material 140, and the shaper aperture 130 is drilled out of the mold material after the mold material has hardened.

As discussed previously, the mold material 140 is selected to be Cerrobend in a preferred embodiment. In addition to being opaque to radiation at selected radiation beam energies, Cerrobend is selected because it does not melt or otherwise adversely affect the insert 135 when in a liquid state and when it solidifies, Cerrobend does not crack or contract to such a degree that the insert 135 loosens within the mold material 140. In other embodiments, other mold materials having the above qualities are employed.

Although specific embodiments of, and examples for, the present invention are described herein for illustrative purposes, various equivalent modifications can be made without departing from the spirit and scope of the invention, as will be recognized by those skilled in the relevant art. The means used to connect the collimator 10 to the radiation source 5 and to connect the beam shaper 2 to the collimator are exemplary and those skilled in the relevant art can create or employ similar connection means under the teachings and concepts of the present invention. Similarly, the means used to releasably couple the components of the jig 200 used to manufacture the beam shaper of the present invention and the geometries of the relevant components are exemplary and those skilled in the relevant art can create or employ similar coupling means under the teachings and concepts of the present invention.

The teachings provided herein of the present invention can be applied to beam shaping devices for use with systems other than the radiation treatment system described above. For example, while the present invention has been generally described in the context of a medical system used to treat tumors, the present invention is equally applicable to other systems which generate radiation beams, such as devices generating laser beams or light beams which may be used in any number of medical or industrial applications.

These and other changes can be made to the invention in light of the above detailed description. In general in the following claims the terms used should not be construed to limit the invention to the specific embodiments disclosed in the specification and the claims but should be construed to include any device that operates in accordance with the claims to provide a shape radiation beam. Accordingly the invention is not limited by the disclosure but instead its scope is to be determined entirely by the following claims.

I claim:

1. A system for shaping a radiation beam exited from a radiation output port of a radiation source, the system comprising:

a mount coupled to the radiation source, the mount having a beam aperture with at least two openings and a tapered inner surface extending between the two openings, one opening being aligned with the radiation output port; and a die having a beam window extending therethrough, the beam window being substantially transparent at at least a selected radiation energy, and a tapered outer surface engaged with the tapered inner surface of the beam aperture.

2. The system of claim 1 wherein the radiation beam is directed toward a target and the beam window has a cross-sectional shape that is substantially a silhouette of the target when the target is viewed from a selected target angle.

3. The system of claim 1 wherein the beam window has a round cross-sectional shape.

4. The system of claim 1, further comprising a tab member located in the die and a tab member aperture located in the mount and releasably engaged with the tab member for positioning the die relative to the beam aperture.

5. The system of claim 1, further comprising a latch member engaging portion and a latch member, the latch member is moved between an engaged position with the latch member engaging the latch member engaging portion and a released position, the latch member engaging portion being located on the die and the latch member being located adjacent to the beam aperture.

6. The system of claim 1 wherein the tapered inner surface of the beam aperture and the tapered outer surface of the die are conical.

7. The system of claim 1 wherein the tapered outer surface of the die is shaped to slideably engage the tapered inner surface of the beam aperture.

8. A die device for shaping a radiation beam produced by a radiation source, the radiation beam passing through a beam aperture in the radiation source toward a selected target, the device comprising a die body having a substantially tapered outer surface tapering from a narrow end to a wide end, and a beam window extending therethrough from the narrow end to the wide end, the narrow end being moved into and out of the beam aperture, the tapered outer surface being shaped to engage the beam aperture, the beam window being aligned with the beam aperture when the die engages the beam aperture, the beam window being substantially transparent at at least a selected radiation energy.

9. The device of claim 8 wherein the die aperture has a cross-sectional shape that is substantially a silhouette of the target when the target is viewed from a selected target angle.

10. The device of claim 8 wherein the die aperture has a round cross-sectional shape.

11. The device of claim 8 wherein the beam aperture has a tapered internal surface, the tapered outer surface of the die body being shaped to engage the tapered internal surface of the beam aperture.

12. The device of claim 8, further comprising a tab member located in the die device and a tab member aperture located in the beam aperture and releasably engaged with the tab member for positioning the die device relative to the beam aperture.

13. The device of claim 8, further comprising a latch member engaging portion and a latch member, the latch member is moved between an engaged position with the latch member engaging the latch member engaging portion and a released position, the latch member engaging portion being located on the die device and of the latch member being located adjacent to the beam aperture.

14. The device of claim 8 wherein the beam aperture has a conical internal surface and the tapered outer surface of the die body is conical.

15. The device of claim 8 wherein the tapered outer surface of the die body is shaped to slideably engage the beam aperture.

16. A die device for shaping a radiation beam, the radiation beam passing through a beam aperture toward a selected target, the device comprising a die body having a substantially tapered outer surface tapering from a narrow end to a wide end, and a die aperture extending therethrough from the narrow end to the wide end, the narrow end being moved into and out of the beam aperture, the tapered outer surface being shaped to engage the beam aperture, the die aperture being aligned with the beam aperture when the die engages the beam aperture, the die body being substantially opaque at at least a selected radiation energy.

17. The device of claim 16 wherein the die body has an outer shell, the tapered outer surface of the die body being an outer surface of the outer shell, the outer shell having a shell aperture therethrough that is substantially coaxial with the die aperture.

18. The device of claim 16 wherein the die body has an outer shell, the tapered outer surface of the die body being an outer surface of the outer shell.

19. The device of claim 16 wherein the die aperture has a round cross-sectional shape.

20. The device of claim 16 wherein the die aperture has a cross-sectional shape that is substantially a silhouette of the target when the target is viewed from a selected target angle.

21. The device of claim 16, further comprising an aperture insert shaped to fit within the die aperture, the aperture insert being transparent at at least the selected radiation energy to permit radiation to pass therethrough.

22. The device of claim 16 wherein the beam aperture has a tapered internal surface, the tapered outer surface of the die body being shaped to engage the tapered internal surface of the beam aperture.

23. The device of claim 16, further comprising a tab member located in the die device and a tab member aperture located in the beam aperture and releasably engaged with the tab member for positioning the die device relative to the beam aperture.

24. The device of claim 16, further comprising a latch member engaging portion and a latch member, the latch member is moved between an engaged position with the latch member engaging the latch member engaging portion and a released position, the latch member engaging portion being located on the die device and the latch member being located adjacent to the beam aperture.

25. The device of claim 16 wherein the beam aperture has a conical internal surface and the tapered outer surface of the die body is conical.

26. The device of claim 16 wherein the tapered outer surface of the die body is shaped to slideably engage the beam aperture.

27. A die device used with a collimator of a radiation therapy apparatus, the collimator having a beam aperture with at least two openings and a tapered inner surface extending between the two openings, the die device shaping a radiation beam emitted by the radiation therapy apparatus through the collimator and comprising:

a die shell having an inner surface defining an interior area and a tapered outer surface tapering from a narrow end to a wide end, the tapered outer surface being shaped to engage the tapered inner surface of the collimator;

an insert element positioned within the interior area of the die shell, extending between the narrow end and the wide end of the die shell, the insert element being of a material which is substantially transparent at at least a selected radiation energy; and a radiation blocking element positioned between the insert element and the inner surface of the die shell and being of a material which is substantially opaque at at least the selected radiation energy.

28. The device of claim 27 wherein the insert element has a cross-sectional shape that is substantially the shape of a radiation therapy target when the target is viewed from a selected angle.

29. The device of claim 27 wherein the tapered inner surface of the aperture and the tapered outer surface of the die shell are conical.

30. The device of claim 27 wherein the tapered outer surface of the die shell is shaped to slideably engage the tapered inner surface of the beam aperture.

31. A radiation therapy device for transmitting a radiation beam to a target, comprising:

a positioning bed for positioning the target;

a radiation beam source for generating a radiation beam, the radiation beam source being movable relative to the target and having a beam aperture therein for directing the radiation beam toward the target; and a die device for shaping the radiation beam, the device having a die body with a tapered outer surface tapering from a narrow end to a wide end, and a die aperture extending therethrough from the narrow end to the wide end, the narrow end being moved into and out of the beam aperture, the tapered outer surface being shaped to engage the beam aperture, the die aperture being aligned with the beam aperture when the die engages the beam aperture, the die body being substantially opaque at at least a selected radiation energy.

32. The device of claim 31 wherein the die aperture has a cross-sectional shape that is substantially a silhouette of the target when the target is viewed from a selected target angle.

33. The device of claim 31, further comprising an aperture insert shaped to fit within the die aperture, the aperture insert being transparent at at least the selected radiation energy to permit radiation to pass therethrough.

34. The device of claim 31 wherein the tapered outer surface of the die body is conical and the beam aperture has a conical internal surface.

35. The device of claim 31 wherein the tapered outer surface of the die body slideably engages the beam aperture.

* * * * *